(12) United States Patent
Cohen et al.

(10) Patent No.: US 7,572,470 B2
(45) Date of Patent: Aug. 11, 2009

(54) LICORICE EXTRACT FOR USE AS A MEDICAMENT

(75) Inventors: Luba Cohen, Kiriyat Yam (IL); Michael Aviram, Haifa (IL)

(73) Assignee: Ready-Made 37 Ltd., Tel-Aviv (IL)

( * ) Notice: Subject to any disclaimer, the term of this patent is extended or adjusted under 35 U.S.C. 154(b) by 184 days.

(21) Appl. No.: 09/955,933

(22) Filed: Sep. 20, 2001

(65) Prior Publication Data

US 2002/0037332 A1    Mar. 28, 2002

(30) Foreign Application Priority Data

Sep. 21, 2000    (IL) .................................... 138603

(51) Int. Cl.
*A61K 36/48* (2006.01)
*A01N 65/00* (2006.01)

(52) U.S. Cl. ...................................... 424/757; 424/725

(58) Field of Classification Search ................. 435/410, 435/390; 424/774, 93.4, 725, 757
See application file for complete search history.

(56) References Cited

U.S. PATENT DOCUMENTS 3,953,423 A * 4/1976 Hadhanyi
4,163,067 A * 7/1979 Hartung
6,280,776 B1 * 8/2001 Sha et al. ..................... 424/728
6,136,349 A1 * 10/2008 Karppanen et al. ............. 426/2

2001/0031744 A1 * 11/2001 Kim et al. ..................... 514/54

OTHER PUBLICATIONS

Fuhrman, Bianca et al., The American Journal of Clinical Nutrition; vol. 66, pp. 267-275 (1997).
Michael Aviram; European Journal of Clinical Chemistry and Clinical Biochemistry, vol. 34, 1996, pp. 599-608.
Jacob Vaya et al.; Free Radical Biology & Medicine, vol. 23, No. 2, 1997, pp. 302-313.
Paula A. Belinky et al.; Free Radical Biology & Medicine, vol. 24, No. 9, Jun. 1998, pp. 1419-1429.
Paula A. Belinky et al.; Atherosclerosis, vol. 137, No. 1, Mar. 1998, pp. 49-61.
Mira Rosenblat et al.; Journal of Biological Chemistry, vol. 274, No. 20, May 14, 1999, pp. 13790-13799.

* cited by examiner

*Primary Examiner*—David M. Naff
*Assistant Examiner*—Deborah K. Ware (57) ABSTRACT

Described are a plurality of risk factors that may be treated and conditions that may be prevented and treated by administering to a patient a preparation containing a licorice extract, which is water insoluble and free from glycyrrhizinic acid. Risk factors that may be lowered include hypertension, high blood glucose concentration, LDL susceptibility to retention, LDL susceptibility to aggregation, blood total cholesterol and LDL levels, and blood tryglicerides and VLDL concentration. Conditions and diseases that may be treated according to the invention include aterosclerotic diseases, hypertension, cardiovascular diseases, chronic renal failure, carotid artery stenosis, coronary heart diseases, hypercholesterolemia, and hypertriglyceridemia.

18 Claims, 10 Drawing Sheets

LICORICE EXTRACT FOR USE AS A MEDICAMENT

FIELD OF THE INVENTION

This invention relates to pharmaceutical and nutraceutical compositions that contain licorice extract.

BACKGROUND OF THE INVENTION

Licorice roots, which consist of the dried unpeeled roots of Glycyrrhiza are widely used in Asia as a sweetener and a spice. Licorice root has also been used medically for more than 3000 years, and a wide range of therapeutic uses have been ascribed thereto. Glycyrrhizinic acid, contained in licorice root, was attributed several pharmacological activities, such as anti-bacterial, anti-viral, anti-inflammatory, anti-allergic and anti-hepatotoxic activity. However, the traditional licorice extracts, and in particular glycyrrhizinic acid, were also shown to cause hypertension, and this severe side effect considerably reduced their use.

Recently, Fuhrman et al. showed that a certain ethanolic extract of licorice is useful in inhibition of LDL oxidation. [Fuhrman et al., The American Journal of Clinical Nutrition, 66, pp. 267-75 (1997)]. This very same study, however, did not find that the consumption of that licorice extract by humans causes any significant influence on plasma cholesterol, LDL concentration, or any other medical characteristic examined.

SUMMARY OF THE INVENTION

The present invention is based on the finding that a licorice extract similar to that used by Fuhrman et al. is useful in decreasing in human subjects the blood pressure, blood glucose concentration, blood total cholesterol and LDL levels, and blood tryglicerides and VLDL concentration. Other findings that led to the present invention are that licorice extract consumption reduces the susceptibility of human blood serum LDL to two heterogenic modifications, namely: retention and aggregation. The licorice extract that was found to bring to these results is characterized by being water-insoluble and free from glycyrrhizinic acid.

In the following, blood pressure, blood cholesterol and LDL levels, blood tryglicerides and VLDL concentration, blood glucose concentration, and serum LDL susceptibility to retention and aggregation will be named generally "risk factors", since they are related to the risk of cardiovascular diseases.

Thus, the present invention provides a pharmaceutical or neutraceutical preparation for lowering at least one of the following risk factors: blood pressure, glucose concentration, blood cholesterol and LDL levels, blood tryglicerides and VLDL concentration, and serum LDL susceptibility to retention and aggregation, said preparation comprising licorice extract, which is water-insoluble and free from glycyrrhizinic acid.

Preferably, the pharmaceutical or neutraceutical composition of the invention is for lowering at least one of the following risk factors: blood pressure, blood glucose concentration, susceptibility of serum LDL to retention, and susceptibility of serum LDL to aggregation.

Most preferably the pharmaceutical or neutraceutical composition of the present invention is for lowering at least one of the following risk factors: blood pressure and glucose concentration.

According to another aspect, the present invention provides licorice extract, which is water-insoluble and free from glycyrrhizinic acid, for use in the prevention and/or treatment of at least one of the following conditions and diseases: inflammation, hypertension, diabetes, chronic renal failure, atherosclerotic diseases, carotid artery stenosis, coronary heart diseases, hypercholesterolemia, and hypertriglyceridemia.

Preferably, the use according to the invention is in the prevention and/or treatment of at least one of the following conditions: hypertension, diabetes, chronic renal failure, and inflammation.

The term prevention means reduction of the risk of having the condition or the disease, while the term treatment means slowing down the development of the condition or the disease or relieving at least one symptom thereof.

The invention also provides the use of licorice extract, which is free from glycyrrhizinic acid, in the preparation of a medicament for preventing or treating any of the conditions and diseases mentioned above.

The invention also provides a pharmaceutical or neutraceutical immuno-potentiator comprising a licorice extract, which is water-insoluble and free from glycyrrhizinic acid. The immuno-potentiating value of the extract may be deduced from its ability to reduce the susceptibility of human serum to LDL aggregation.

According to another aspect of the present invention there is provided a method for treating hypertension, diabetes, chronic renal failure, cardiovascular diseases, carotid artery stenosis, atherosclerotic diseases, and coronary heart diseases in a subject, comprising administering to said subject a therapeutically effective amount of a licorice extract that is water-insoluble and free of glycyrrhizinic acid.

Preferably, the method of the invention is for treating hypertension, diabetes, and chronic renal failure, and most preferably hypertension.

BRIEF DESCRIPTION OF THE DRAWINGS

In order to understand the invention and to see how it may be carried out in practice, a detailed description of some experimental results will now be given, by way of non-limiting example only, with reference to the accompanying drawings, in which.

DETAILED DESCRIPTION OF THE INVENTION

Preparation of an Extract Suitable for use According to the Present Invention 1 kg raw Licorice root was ground to obtain slices of about 0.5 to 2 cm length and dried. The dry ground root was steeped in 5 liter absolute ethanol at room temperature, stirred for 5 hours, and filtered. The ethanol was evaporated and the resultant residue was dried to constant mass at 85° C. to give 30 gr of product.

The product, hereinafter referred to as licorice extract, was then pulverized to give fine reddish brown powder that is practically insoluble in water and with no traceable amount of glycyrrhizinic acid. The powder was conventionally encapsulated and given to the volunteers in the experiment described bellow.

Some notes on the above procedure are in place: licorice extracts of similar health promoting effects, even if in other concentrations and required dosages, may be obtained also with other extracting solutions like acetone, ethyl acetate or hexane. Ethanol was found by the inventors to give the extract with the highest yield and activity. In any case, it is important that the raw material is dried before the extraction and that the extraction is carried out in a dry solvent. Otherwise, the product will be somewhat water-soluble, and obtaining the extract of the invention will necessitate expensive and complicated processes for removing the water-soluble portions of the extract.

Experiments Demonstrating Therapeutic Potential of the Extract Prepared as Described Above.

Twelve adult hypercholesterolemic patients consumed for one month 100 mg licorice extract per day. The risk factors defined above were measured in these patients before and after licorice consumption, and compared. The results are shown in FIGS. 1 to 10.

In FIGS. 1 to 8 and 10 the X axis values are of the measured risk factor before licorice consumption, the Y axis values are of the measured risk factor after licorice consumption, and the straight line is the equation Y=X. Every point bellow this line represents (at least one) patient in whom the measured risk factor after licorice consumption was lower then before.

Figure 1:
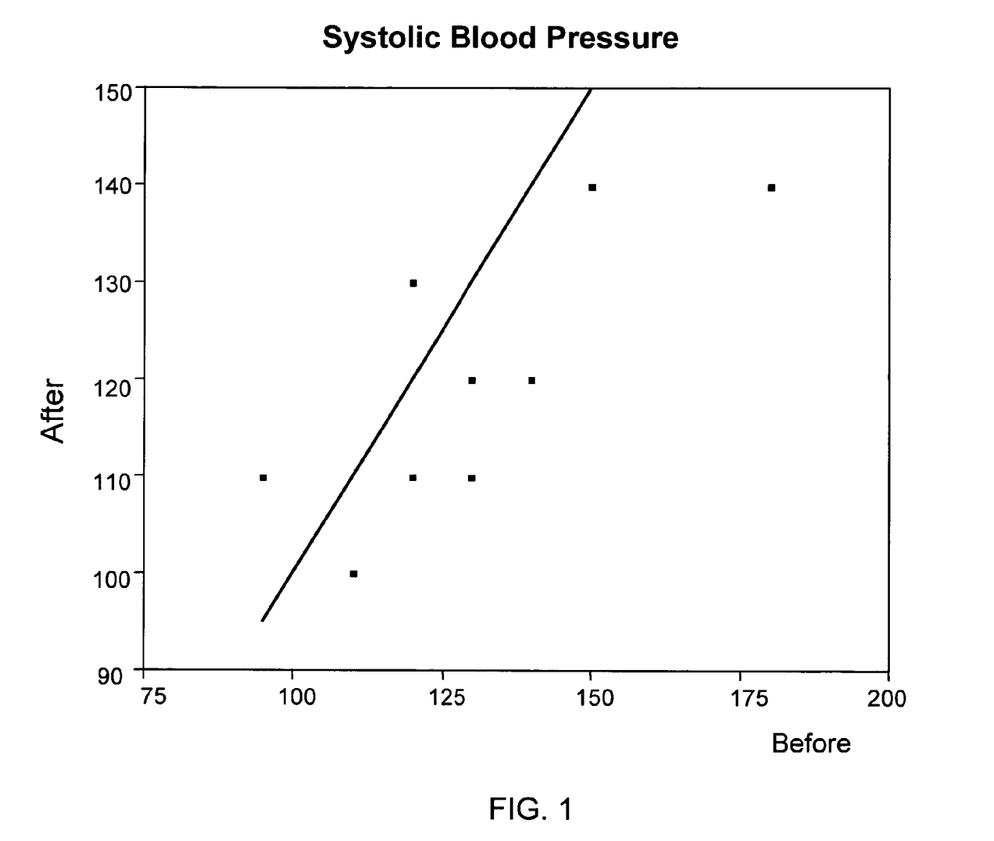
FIG. 1 is a graph showing the effect of licorice extract on systolic blood pressure.
Figure 2:
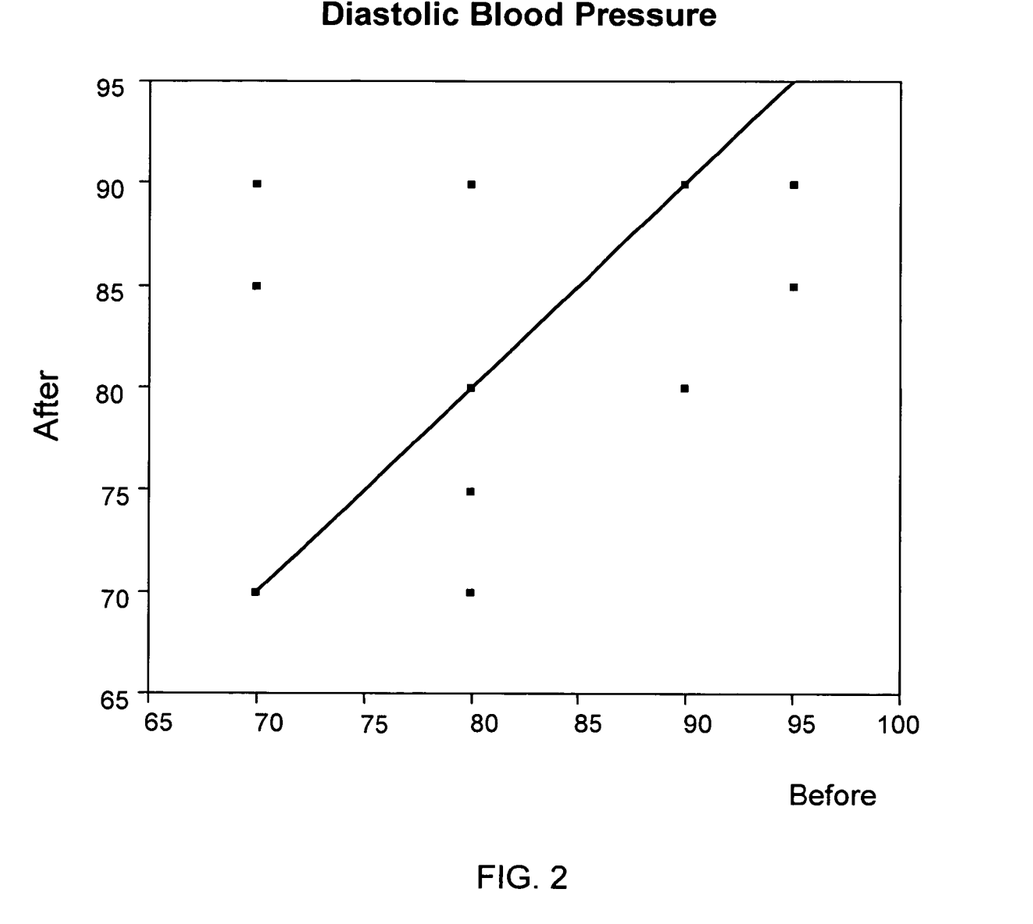
FIG. 2 is a graph showing the effect of licorice extract on diastolic blood pressure.

FIG. 1 shows that ten out of the twelve patients showed a decrease in the systolic blood pressure after licorice consumption. FIG. 2 shows that the diastolic blood pressure of the same 12 patients was not significantly effected by the licorice consumption.

Lowering the blood pressure may be useful in reducing the risk to atherosclerotic diseases and is desirable in the treatment of a variety of disease and conditions, e.g. cardiovascular diseases, chronic renal failure, carotid artery stenosis, and coronary heart diseases, in patients with high blood pressure.

Figure 3:
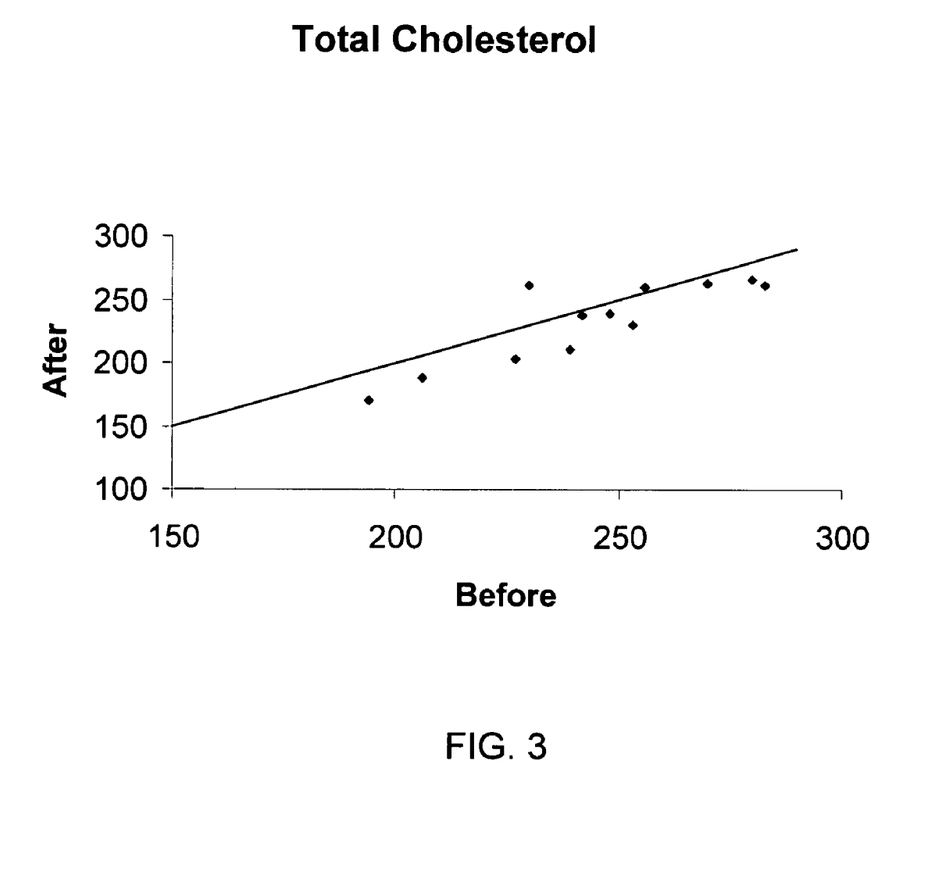
FIG. 3 is a graph showing the effect of licorice extract on cholesterol levels in the blood.
Figure 4:
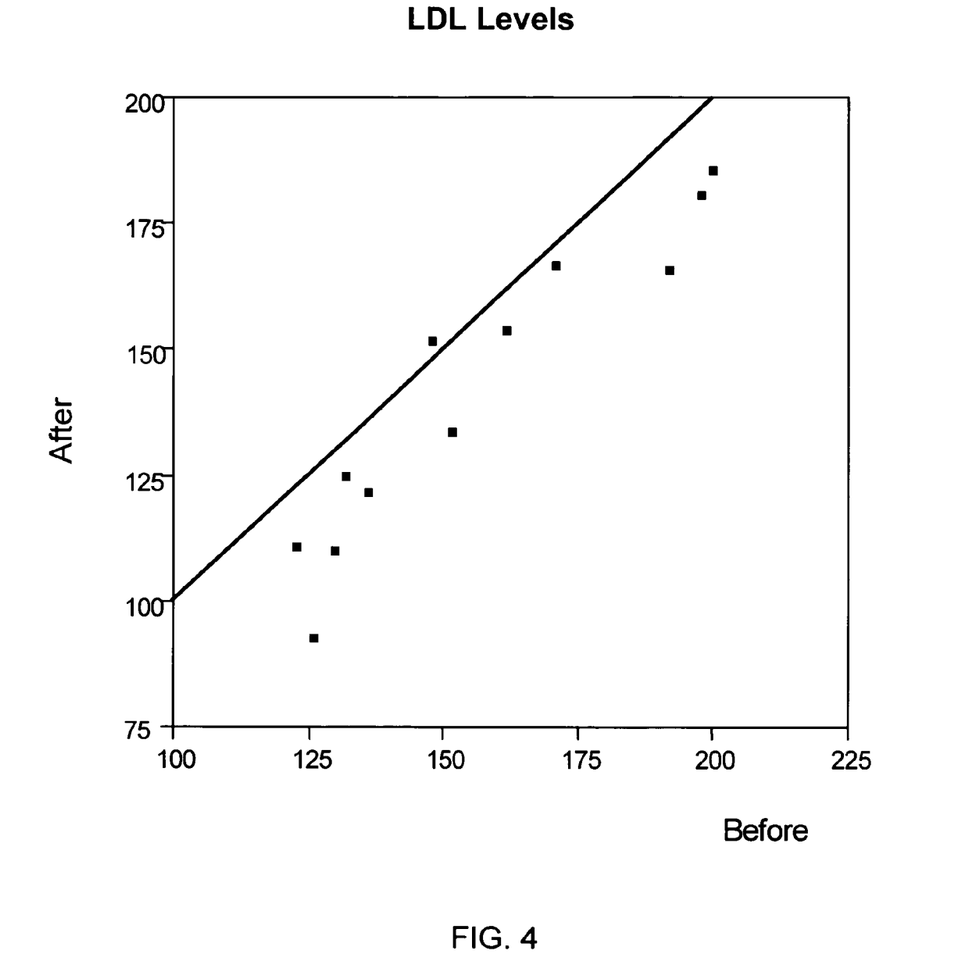
FIG. 4 is a graph showing the effect of licorice extract on LDL levels in the blood.
Figure 5:
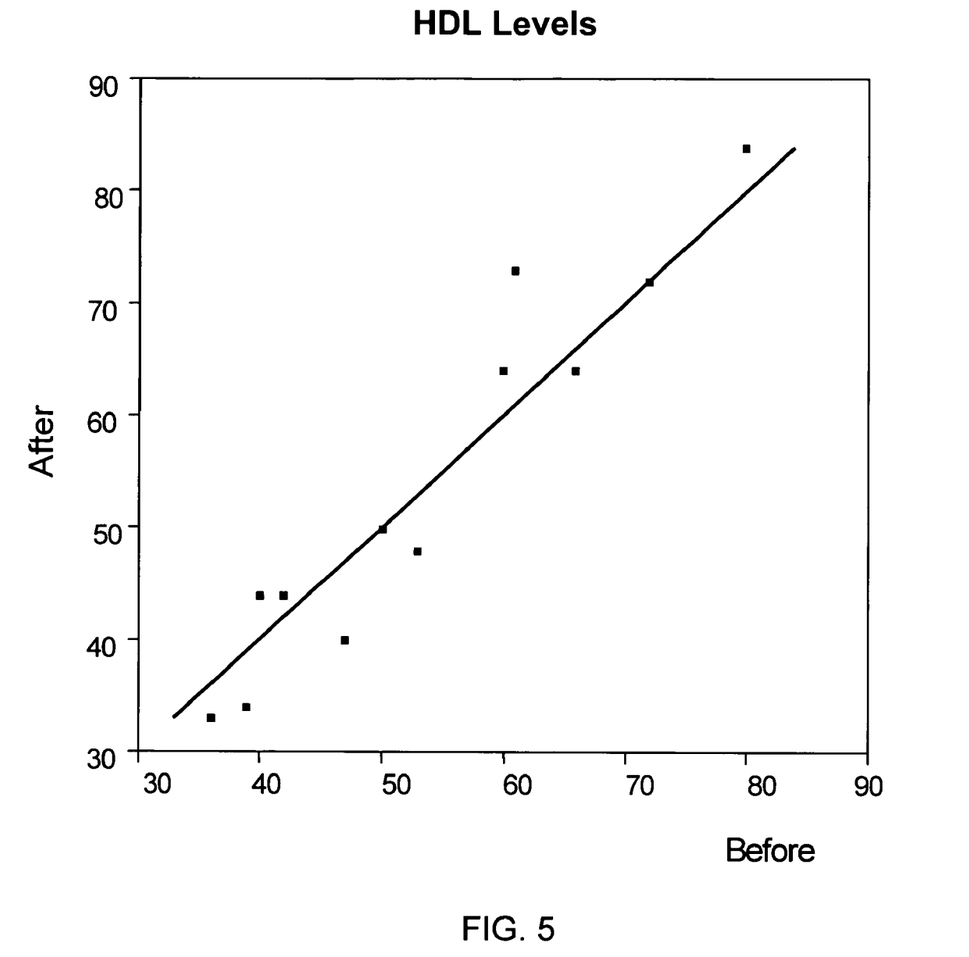
FIG. 5 is a graph showing the effect of licorice extract on HDL levels in the blood.

The graphs in FIGS. 3 and 4 show the cholesterol and LDL levels (measured in mg/dl) in the same patients before and after consuming licorice extract. As shown in the figures, after consumption of licorice extract the cholesterol level decreased in 10 out of 12 patients and the LDL decreased in 11 out of 12. FIG. 5 shows that no significant change of HDL levels was detected after consumption of the licorice extract. As may be deduced from the results shown in FIGS. 3, 4, and 5 most of the decrease in cholesterol is due to a decrease in the LDL level, not in HDL level. Lowering the cholesterol and LDL levels may effect hypercholesterolemic patients to reduce the risk of atherosclerotic diseases and is desirable in the treatment of cardiovascular diseases, chronic renal failure, carotid artery stenosis, and coronary heart diseases in these patients. The simultaneous lowering of the LDL levels and blood pressure that the licorice extract exhibits may be especially beneficial to patients that suffer from both high blood pressure and high LDL levels. On the other hand it makes the licorice extract effective to a wide population, including both hypertension and hypercholesterolemic patients.

Figure 6:
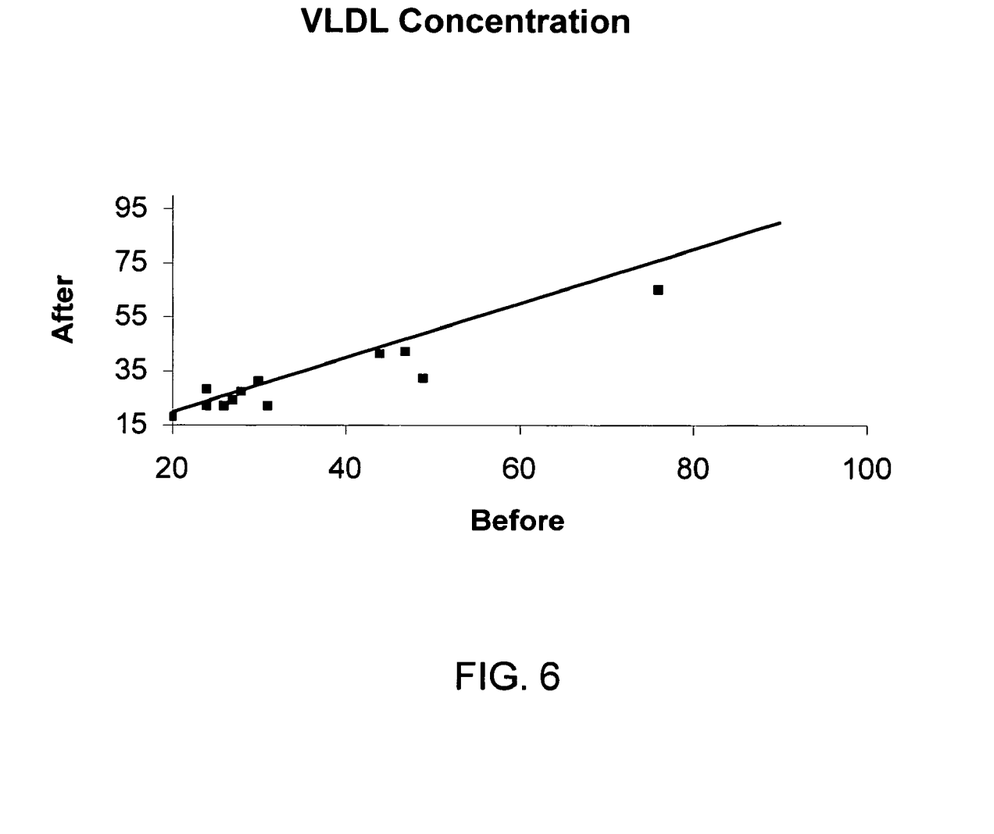
FIG. 6 is a graph showing the effect of licorice extract on VLDL levels in the blood.
Figure 7:
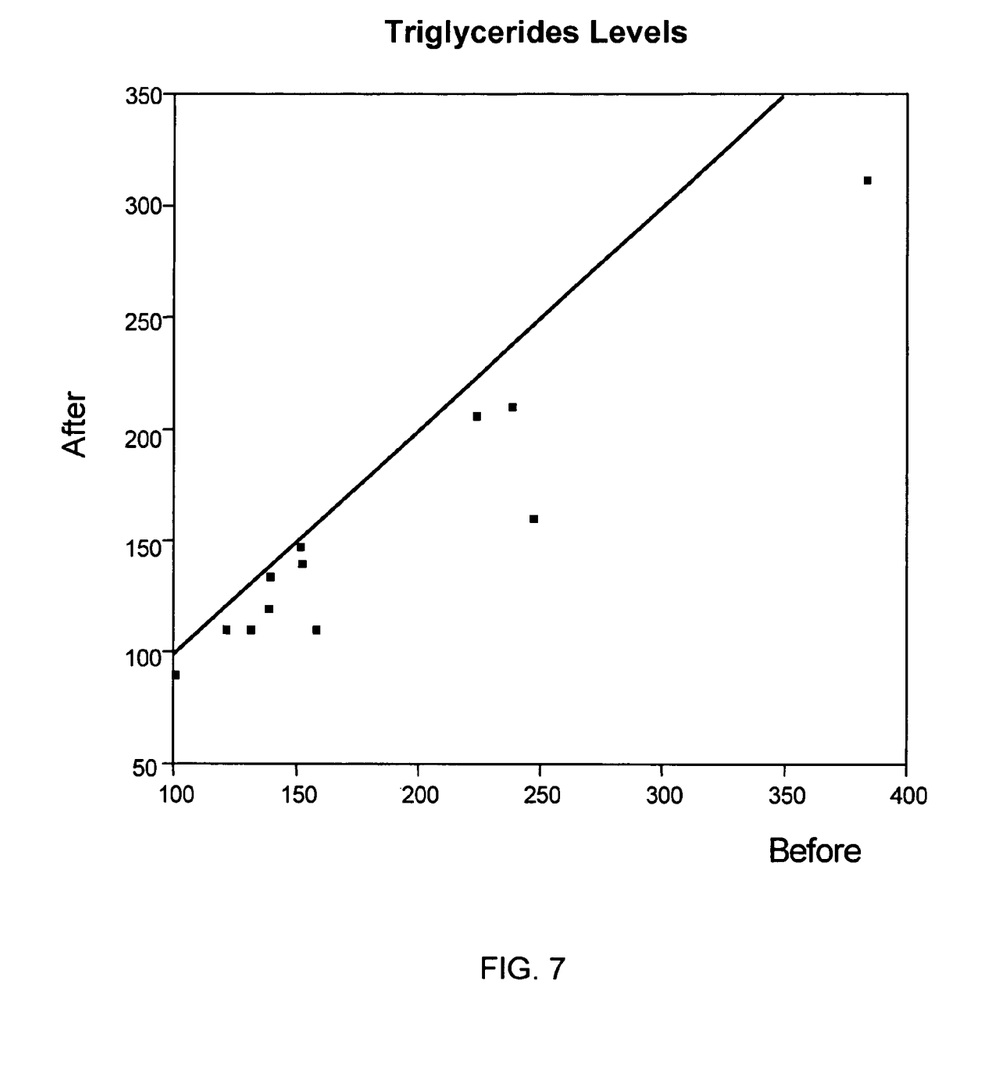
FIG. 7 is a graph showing the effect of licorice extract on triglycerides levels in the blood.

FIGS. 6 and 7 show that after the licorice consumption, all the twelve patients had lower blood concentration of triglycerides than they had prior to this consumption, and 10 out of 12 had lower VLDL blood concentration. Furthermore, the average decrease in the triglycerides level was about 20%, which is remarkable for one month treatment. Lowering the triglycerides and the VLDL concentrations may have beneficial effects as were already mentioned before, and widens even more the population that may benefit from licorice extract consumption. It may also be useful as a single medication to help people that suffer from more than one of the risk factors: high blood pressure, high cholesterol and LDL levels, and high triglyceride concentration.

Figure 8:
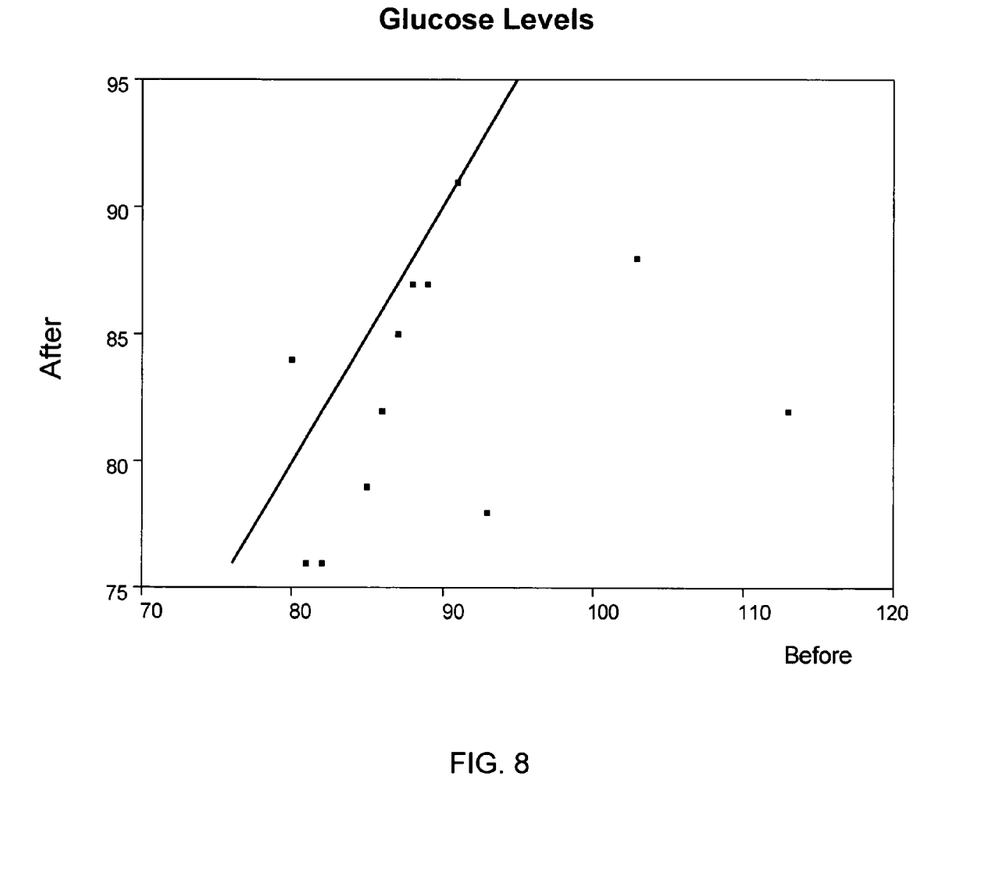
FIG. 8 is a graph showing the effect of licorice extract on glucose levels in the blood.

FIG. 8 shows the effect of licorice extract on blood-glucose. The figure shows that in 10 out of the twelve patients the blood-glucose decreased. Lowering the blood-glucose may reduce the risk to diabetes and its complications, including, for instance, chronic renal failure, blindness, and acceleration of atherosclerotic processes. The combination of lowering the glucose levels in the blood and lowering the blood pressure may be most beneficial to patients that are at high risk to renal failure. The combination of these two effects with the lowering of cholesterol and LDL levels may be beneficial to patients that suffer from any combination of the four risk factors.

Figure 9:
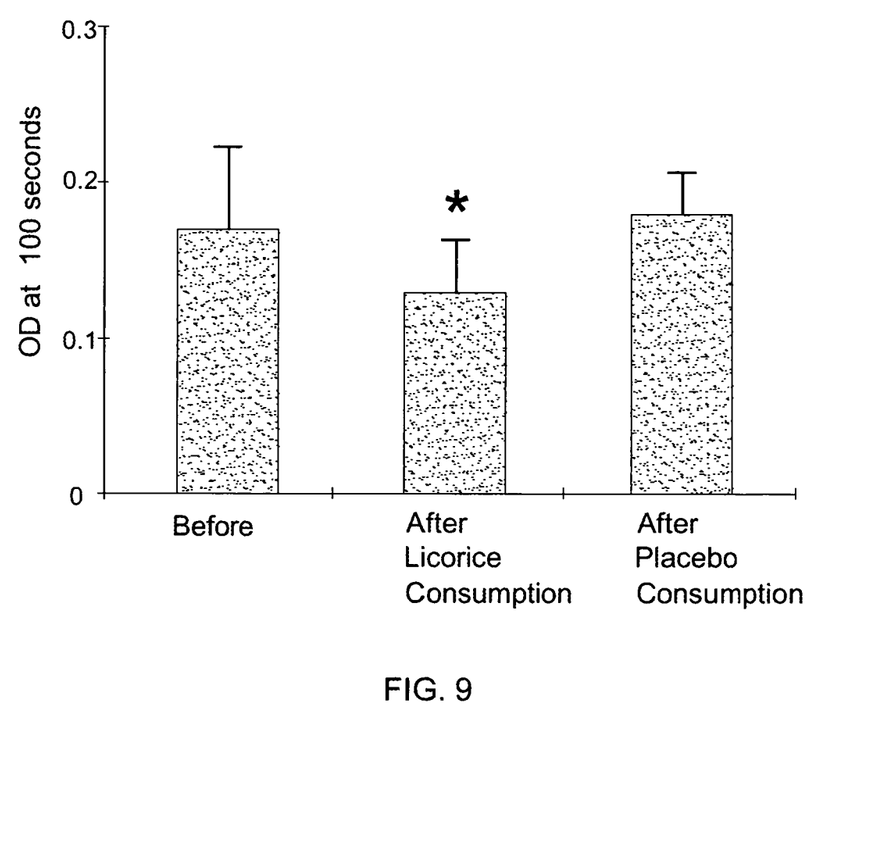
FIG. 9 is a graph showing the effect of licorice extract on serum susceptibility to LDL retention.

FIG. 9 is a graph of the development of serum-LDL optical density at 680 nm during vortexing at a constant strength before licorice consumption, after licorice consumption, and after placebo consumption. The placebo was given for one month after the consumption of the licorice extract. The graph clearly shows that the LDL susceptibility to aggregation was lowered by the licorice consumption and returned to baseline level after licorice intact termination and placebo consumption.

Figure 10:
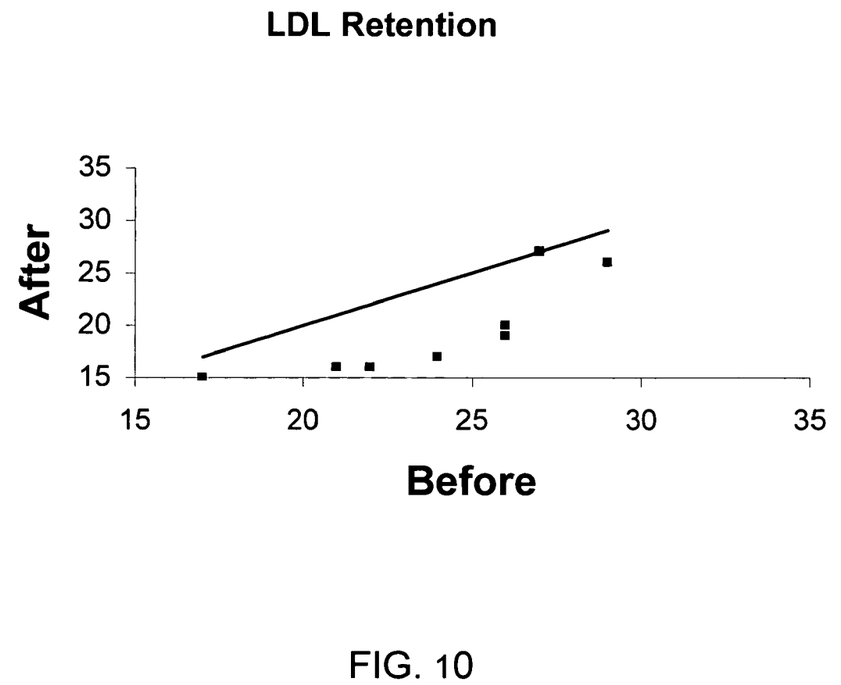
FIG. 10 is a graph showing the effect of licorice extract on serum susceptibility to LDL aggregation.

FIG. 10 shows the effect of licorice extract consumption on LDL retention. The results clearly show the LDL retention was significantly lowered thanks to the licorice extract consumption.

The invention claimed is:

1. A method for lowering at least one risk factor in a patient suffering from said risk factor, comprising
   identifying that said patient suffers from said at least one risk factor; and
   administering to said patient a therapeutically effective amount of a licorice extract which is water-insoluble and free from glycyrrhizinic acid, thereby lowering said risk factor, wherein said at least one risk factor comprises a risk factor selected from the group consisting of high blood pressure, high blood glucose concentration, and high blood triglycerides concentration.

2. The method of claim 1, wherein one of said at least one risk factor is high blood pressure.

3. The method according to claim 1, wherein one of said at least one risk factor is high blood glucose concentration.

4. A method according to claim 1, wherein said patient suffers from at least two risk factors, at least one of which is selected from the group consisting of said high blood pressure, high blood glucose concentration, and high blood triglycerides concentration, and at least one selected from the group consisting of high LDL (low-density lipoprotein) levels, high blood total cholesterol, and high VLDL (very low-density lipoprotein) concentration.

5. A method according to claim 4, for treating a patient suffering from said high blood triglycerides and high LDL (low-density lipoprotein) levels without decreasing the HDL (high density lipoprotein) level of said patient, comprising
administering to said patient a therapeutically effective amount of a licorice extract which is water-insoluble and free from glycyrrhizinic acid, thereby lowering said high blood triglycerides and said high LDL levels without decreasing the HDL level of said patient.

6. The method according to claim 1, comprising obtaining said licorice extract in a method comprising extracting licorice in ethanol.

7. The method according to claim 4, comprising obtaining said licorice extract in a method comprising extracting licorice in ethanol.

8. The method according to claim 5, comprising obtaining said licorice extract in a method comprising extracting licorice in ethanol.

9. The method according to claim 1, wherein said licorice extract dissolves in ethanol.

10. The method according to claim 4, wherein said licorice extract dissolves in ethanol.

11. The method according to claim 5, wherein said licorice extract dissolves in ethanol.

12. The method according to claim 1, wherein one of said at least one risk factor is high blood triglycerides concentration.

13. The method of claim 1, wherein administering to said patient a therapeutically effective amount of a licorice extract consists of administering to said patient a pharmaceutical or nutraceutical preparation, said preparation being free from water-soluble licorice extract.

14. A method for treating a patient suffering from at least one condition, comprising
identifying that said patient suffers from said at least one condition; and
administering to said patient a therapeutically effective amount of a licorice extract which is water-insoluble and free from glycyrrhizinic acid, wherein said at least one condition is selected from the group consisting of hypertension and chronic renal failure.

15. The method according to claim 14, comprising obtaining said licorice extract in a method comprising extracting licorice in ethanol.

16. The method according to claim 14, wherein said licorice extract dissolves in ethanol.

17. The method according to claim 14, wherein one of said at least one condition is hypertension.

18. The method according to claim 14, wherein one of said at least one condition is chronic renal failure.

* * * * *